US 6,652,479 B2

(12) United States Patent
Rasor et al.

(10) Patent No.: US 6,652,479 B2
(45) Date of Patent: Nov. 25, 2003

(54) METHOD AND APPARATUS FOR TRANSCUTANEOUS INFUSION OF CARBON DIOXIDE FOR LOCAL RELIEF OF PAIN AND OTHER AILMENTS

(75) Inventors: Ned S. Rasor, Cupertino, CA (US); Julia S. Rasor, Los Gatos, CA (US)

(73) Assignee: Capnia, Inc., Los Gatos, CA (US)

( * ) Notice: Subject to any disclaimer, the term of this patent is extended or adjusted under 35 U.S.C. 154(b) by 0 days.

(21) Appl. No.: 09/795,648

(22) Filed: Feb. 28, 2001

(65) Prior Publication Data

US 2002/0040205 A1 Apr. 4, 2002

Related U.S. Application Data

(60) Provisional application No. 60/185,495, filed on Feb. 28, 2000.

(51) Int. Cl.$^7$ .......................... A61M 37/00; A61K 9/70
(52) U.S. Cl. ........................................ 604/23; 424/449
(58) Field of Search ................ 604/23, 24; 128/205.28, 128/202.26; 424/43–44, 443–449, 466

(56) References Cited

FOREIGN PATENT DOCUMENTS

| FR | 2 656 218 | * 12/1989 | .......... A61H/33/14 |
| WO | WO 91/08793 A1 | 6/1991 | |
| WO | WO 99/29249 A1 | 6/1999 | |

* cited by examiner

*Primary Examiner*—Weilun Lo
*Assistant Examiner*—Linh Truong
(74) *Attorney, Agent, or Firm*—Jill L. Robinson

(57) ABSTRACT

The invention relates to methods and devices for transcutaneous and transmucosal application of carbon dioxide in the form of a gas and in the form of a capnic solution (such as carbonated water) for the relief of pain, including musculoskeletal disorders, neuralgias, rhinitis and other ailments. Gaseous carbon dioxide is applied to the skin for at least three minutes, and the capnic solution may be held on the skin for at least three minutes, which provides relief of symptoms. The capnic solution may also be sprayed onto mucous membranes such as the nose for relief of symptoms such as allergic rhinitis.

4 Claims, 13 Drawing Sheets

METHOD AND APPARATUS FOR TRANSCUTANEOUS INFUSION OF CARBON DIOXIDE FOR LOCAL RELIEF OF PAIN AND OTHER AILMENTS

CROSS-REFERENCE TO RELATED APPLICATIONS

This application claims the benefit of U.S. Provisional Patent Application No. 60/185,495, filed on Feb. 28, 2000, which is incorporated by reference herein.

BACKGROUND OF THE INVENTION

1. Field of the Invention

This invention relates to methods and apparatus for delivery of carbon dioxide ($CO_2$), and other physiologically active agents to individuals.

Alternative methods and devices for delivering carbon dioxide and other gases to individuals are described in U.S. patent application Ser. No. 09/614,389 filed Jul. 12, 2000 and Ser. No. 09/708,186 filed Nov. 7, 2000, which are incorporated by reference herein. Those applications describe the use of $CO_2$, or other therapeutic gas or agents, and associated transmucosal dispensing apparatus for providing controlled amounts of gas to the nose, mouth and/or eye for use in the relief of headaches, allergic rhinitis and asthma, among other ailments, and for the potentiation of the actions of certain drugs and/or physiologically active agents.

The present invention, however, relates to methods and apparatus for transcutaneous application of $CO_2$ (i.e., applied to the skin) and transmucosal application of $CO_2$ (i.e., applied to a mucous membrane) in both the form of a gas and in the form of aqueous solutions (such as carbonated water).

2. Related Art

Subcutaneous Applications of $CO_2$ $CO_2$ is a known therapeutic agent and subcutaneous application has been found to relieve a variety of ailments.

A West German group conducted a 3-year clinical treatment program involving local subcutaneous injection of gaseous $CO_2$ [A. Grosshans and H. Gensch, Z. gesamte inn. Med., Jahrig. 42 (1987) Heft 23]. The 335 patients treated had the following indications:

1. Cervico-cranial syndrome, in particular pains in the neck, contractions of the neck, headache including migraine and vertigo;
2. Cervico-brachial syndrome;
3. Lumbalgia with and without root-irritation syndrome;
4. Other muscular-skeletal pain conditions (degenerative changes, muscular contractions and others).

The treatments consisted of daily or twice-weekly injections of 100–200 ml of $CO_2$ gas under the skin, in the body regions indicated, for a period of 2–5 weeks (10–15 injections). An ~8 cm diameter gas emphysemum arose with a mild hyperemia of the skin at the injection site which disappeared within 3–5 minutes after the injection. Improvement of the indicated disorder occurred after 4–5 treatments. Of the total patients treated, 171 became difficulty-free or were substantially improved, 157 were improved with some remaining distress and 7 had no improvement.

Mineral Baths

Effervescent mineral water baths have been known from antiquity to the present as being effective for relieving musculoskeletal, neural and rheumatic pain. In general, it has been assumed that the dissolved mineral components were responsible for the therapeutic effects of the baths. However, the experimental evidence developed by the inventors suggests that the effectiveness of such baths arises from the high $CO_2$ content of the mineral water rather than from its other dissolved components.

SUMMARY OF THE INVENTION

The inventors discovered that results similar to those obtained by subcutaneous injection of $CO_2$ could be obtained by transcutaneous application of $CO_2$. This application could be made either by applying the $CO_2$ in the form of gas, or alternatively, in the form of aqueous solutions (i.e., carbonated water).

Application of the $CO_2$ may be transcutaneous (through the skin) or transmucosal (through a mucous membrane). For example, gaseous $CO_2$ or an aqueous solution of $CO_2$ may be applied to external skin surfaces for relief of various ailments. Furthermore, an aqueous solution of $CO_2$ may be sprayed into the nose, mouth and/or upper respiratory passages for relief of various ailments as an alternative to the application of gaseous $CO_2$ which was described in U.S. patent applications Ser. No. 09/614,389 and 09/708,186.

DETAILED DESCRIPTION OF THE DRAWINGS

Transcutaneous application of gaseous $CO_2$ has been found to relieve ailments previously treatable by subcutaneous injections of gaseous $CO_2$.

Application of Gaseous $CO_2$

One of the inventors undertook tests between Jan. 3 and Feb. 6, 2000 to determine whether beneficial results obtained by subcutaneous injection of $CO_2$ could be obtained by the less invasive means of transcutaneous diffusion. Since the above-cited subcutaneous treatments occurred over periods of days to weeks, the inventor reasoned that continuous chronic infusion, via a transcutaneous "$CO_2$ patch", might give equivalent relief of distress if the period of the 100–200 ml dose infusion was applied over 24 hours or more, i.e., at a rate as low as ~0.1 mil/minute.

Figure 1:
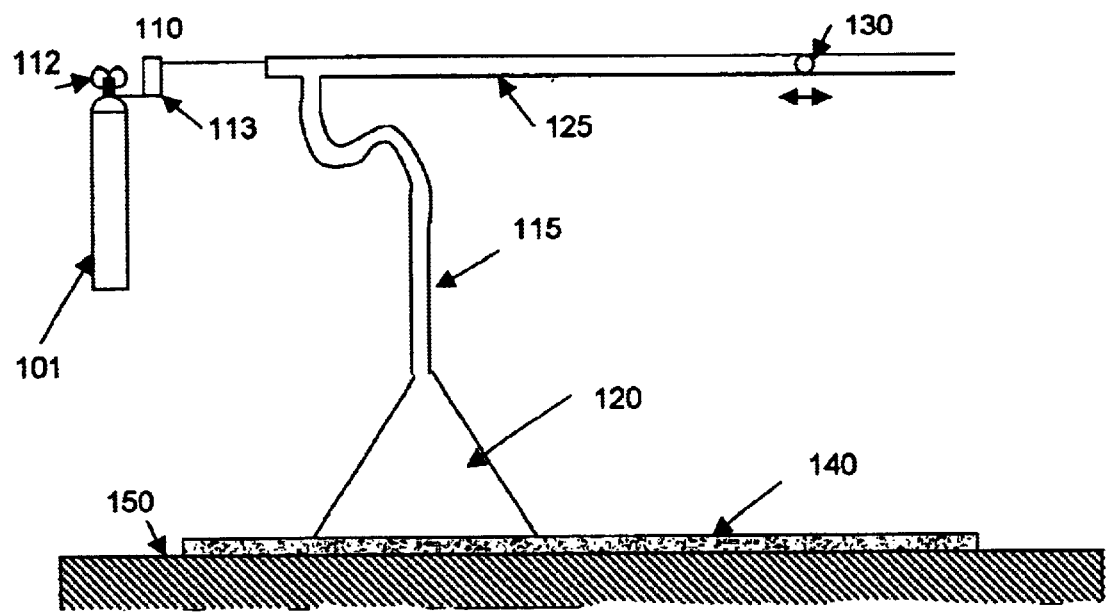
FIG. 1 shows a device used to test absorption of carbon dioxide.

To determine the inherent rate of absorption and diffusion of $CO_2$ in a "passive" aqueous medium a preliminary in vitro experiment was performed. The apparatus and method employed for measuring the rate of $CO_2$ absorption by a surface is illustrated in FIG. 1. The device was placed on a table top 150, and comprised a source of $CO_2$ in the form of a cylinder 101 and a flow regulator 110, including a pressure regulator 112 and flow meter 113. Polyethylene tubing 115 of approximately 0.2 $cm^2$ lumen connected the cylinder 101 to a glass funnel 120 having a maximum area of 80 $cm^2$. An additional length of tubing 125 was used for measurement of changes in gas volume. This gas volume measurement means used in the experiment could be eliminated in a device intended to administer $CO_2$ to a patient's skin surface. The entire system was purged of air by prolonged $CO_2$ flow. The additional length of tubing 125 was purged first, then a bolus of low-volatility (forepump) oil 130 was inserted into its open end and the end plugged. The funnel 120 was then purged with its open end resting on a portion of the selected test surface 140 immediately adjacent to the portion to be tested, and with the purge flow escaping at its edge. At zero time the purge flow was terminated, the plug in the tube 125 end was removed and the funnel was slid onto the test portion of the surface without breaking the seal between the funnel edge and the wet surface. The displacement of the oil bolus 130 within the 0.20 $cm^2$ lumen of the tube 125 was then observed as $CO_2$ gas was removed from the closed system via absorption in the surface 140; i.e., each cm of displacement corresponded to absorption of 0.20 cc of gas by 80 $cm^2$ of test surface.

As a control, the system was first tested by placing the funnel 120 on a non-absorbing test surface 140 without water. No movement of the bolus 130 occurred, which indicated that there was no significant absorption or evolution of gas within the system.

Figure 2:
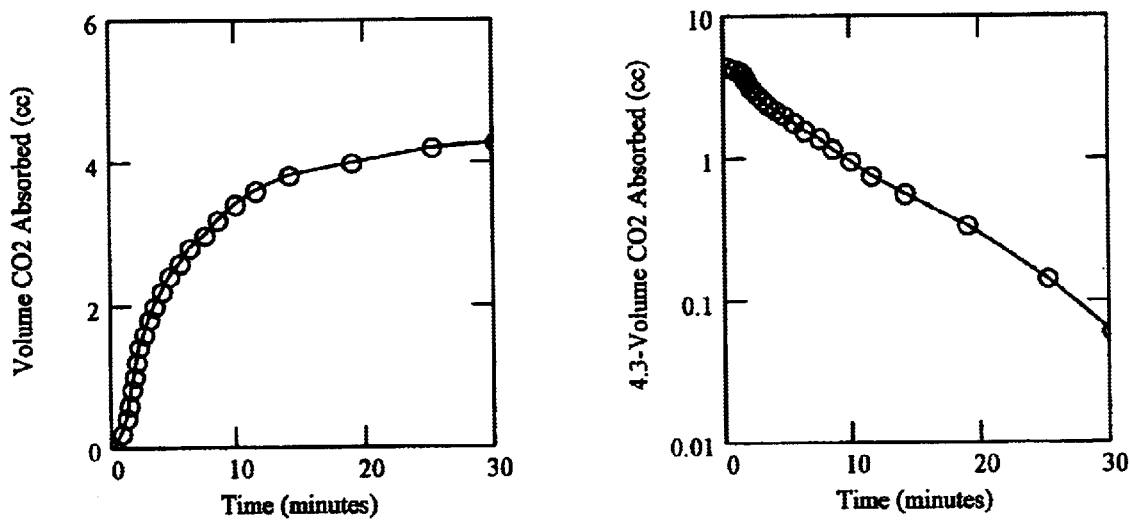
FIG. 2 shows the carbon dioxide absorbed by a wet paper towel in an experiment using the device of FIG. 1.

Next, the funnel was placed on test surface 140 of a 0.4-mm thick water-soaked paper towel having about the same thickness as skin. FIG. 2 shows the observed rate of absorption of gaseous $CO_2$ into the surface of the towel, i.e., a monotonic quasi-exponential approach of the absorbed gas volume to the amount apparently required to saturate the water in the towel with $CO_2$. The near linearity of the second (logarithmic) plot in FIG. 2 shows that the volume of gas changes quasi-exponentially as saturation is approached. The observed initial rate of absorption determined from several such tests fell in the range 0.6–1.2 ml/min, and saturation occurred at 4–10 ml, for the 80-$cm^2$ area test surface. If the vascular bed of the skin suppresses saturation by removing $CO_2$ as fast as it diffuses into the skin, these rates would suggest that a 100–200 cc transcutaneous dose $CO_2$ would be delivered in 1½ to 5½ hours. The inventors thus concluded that the rate was sufficient for a "$CO_2$ patch" to be feasible. Significantly, the time constant for the exponential saturation was found to be about three to five minutes, which was about the same as the reported time for disappearance of the gas emphysemum in the previously described subcutaneous gaseous $CO_2$ injections.

Figure 3:
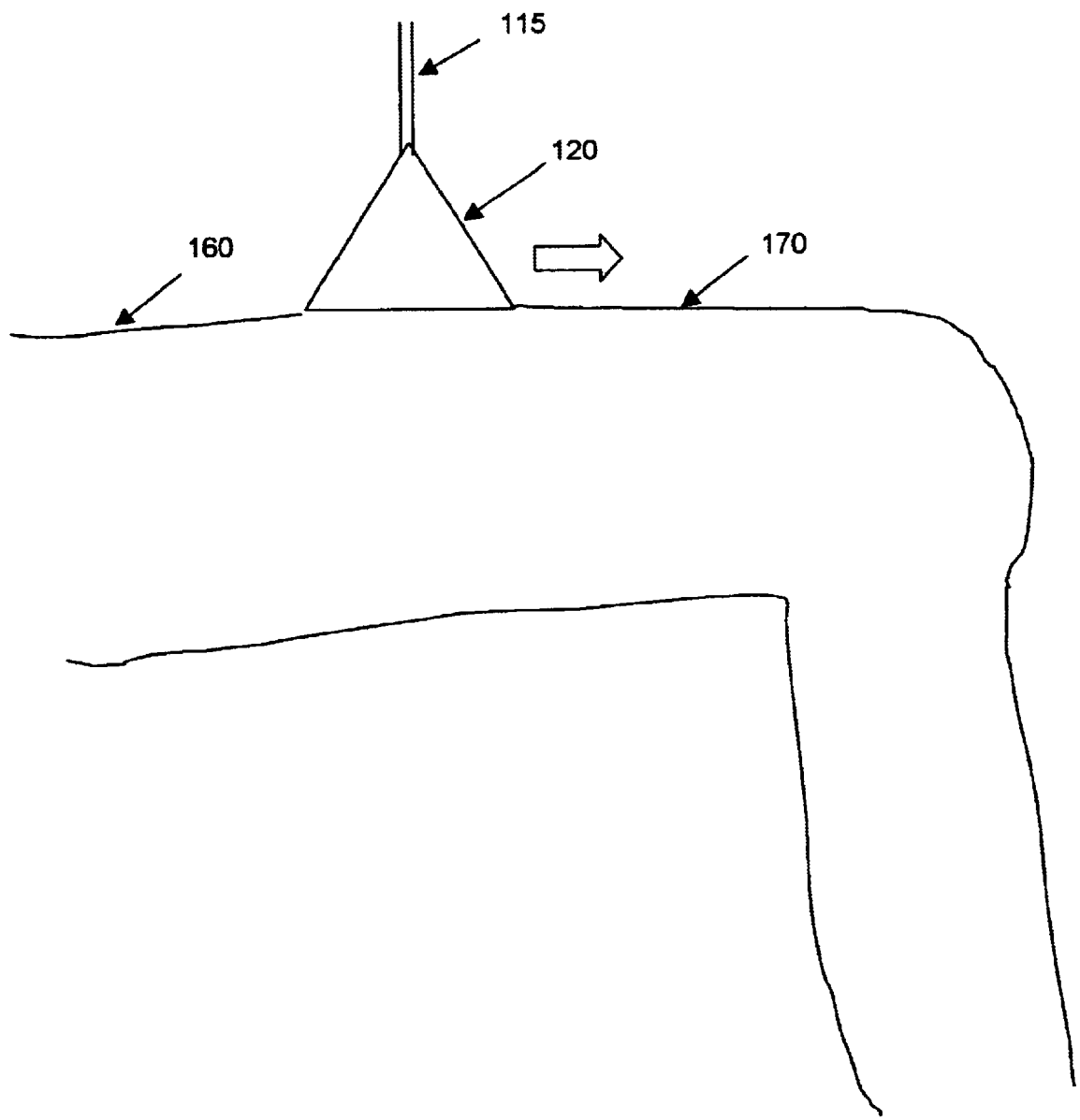
FIG. 3 shows the device of FIG. 1 used on a human subject.

Finally, as shown in FIG. 3, an attempt was made to measure the rate of transcutaneous absorption of $CO_2$ into a human body using the same system. An area of skin on the right anterior thigh sufficiently large for two positions of the funnel 120 applicator was washed thoroughly and soaked with water for fifteen minutes. The funnel 120 was purged of air by prolonged $CO_2$ flow (for about 10 minutes) while seated on the wet skin in the upper thigh position 160, and then was slid to the lower thigh position 170 at zero time. In several such tests, each over a period of about 10 minutes, no significant flow was observed, which suggested that there was no measurable absorption of $CO_2$ by the skin within the sensitivity of the method. In other words, it appeared that less than <0.1 ml of gas was absorbed. However, after all such tests, when the funnel 120 containing $CO_2$ was removed, a hyperemia was observed over the region of skin in contact with $CO_2$, corresponding to that of moderately severe sunburn. This reddening requires about three to five minutes to develop in contact with $CO_2$, and a similar period to subside after removal of the $CO_2$. There were no observed aftereffects. In a control experiment, the inventors found that no reddening of the skin appeared when only air was applied for ten minutes. Therefore, the inventors concluded that some quantity of $CO_2$, sufficient to cause the observed vascular effects, must have diffused into the skin. Therefore, the inventors continued with their experiments to determine if a transcutaneous application of $CO_2$ would reduce local pain.

Application of Capnic Solutions
Treatment of Pain by Transcutaneous Infusion of $CO_2$ To determine if pain could be treated using gaseous $CO_2$, a 73-year-old female subject was selected, who was diagnosed with fibromyalgia. The subject was experiencing chronic, highly localized pain over an area of approximately two to three centimeters in diameter on both her outer thighs. The area was exquisitely sensitive to touch. In addition to the localized pain, the subject also had more general pain along the path of the sciatic nerve which occurred identically in both legs.

Figure 4:
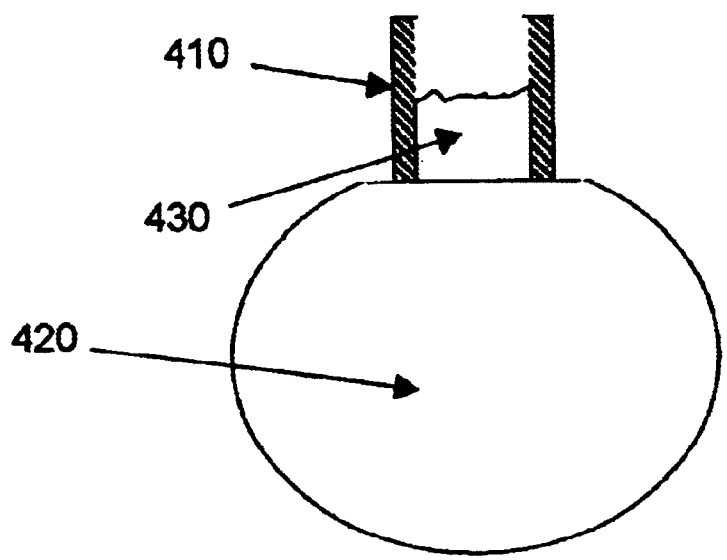
FIG. 4 shows a device for applying carbonated water to a selected portion of a subject's external skin surface.

The experiment employed an open-cylinder procedure shown in FIG. 4. The interior diameter of the cylinder 410 measured approximately 5 cm. The cylinder was placed over the area of localized pain on one thigh 420. The cylinder was then filled approximately 2 cm deep with carbonated water 430. After the application of carbonated water 430, the area of application was observed to be reddened to the degree described above in the Preliminary Experiments section when gaseous $CO_2$ was applied to the skin. In this experiment a PVC pipe was used as the cylinder, although in practice other materials could be used, provided that the resulting device was able to hold the water in position over the treatment area for the desired time.

The subject stated, within 2–3 minutes after the application of the carbonated water, that the localized pain was fully relieved, and that the general pain was partially suppressed over about a 15-cm length along the sciatic nerve path in her thigh. The pain in the other leg was not affected. The device was then removed from the subject's thigh. About 1½ hour after the application, the subject stated that the localized pain had returned somewhat, but still was far less than that in the other leg. The general pain then was about the same in both legs.

In part as a result of the foregoing experiment, the inventors believe that carbonated water baths may be used effectively for treatment of musculoskeletal, neural and other rheumatic pains by immersion of the affected portions of the body or the whole body into fresh carbonated water for at least three minutes.

Figure 5:
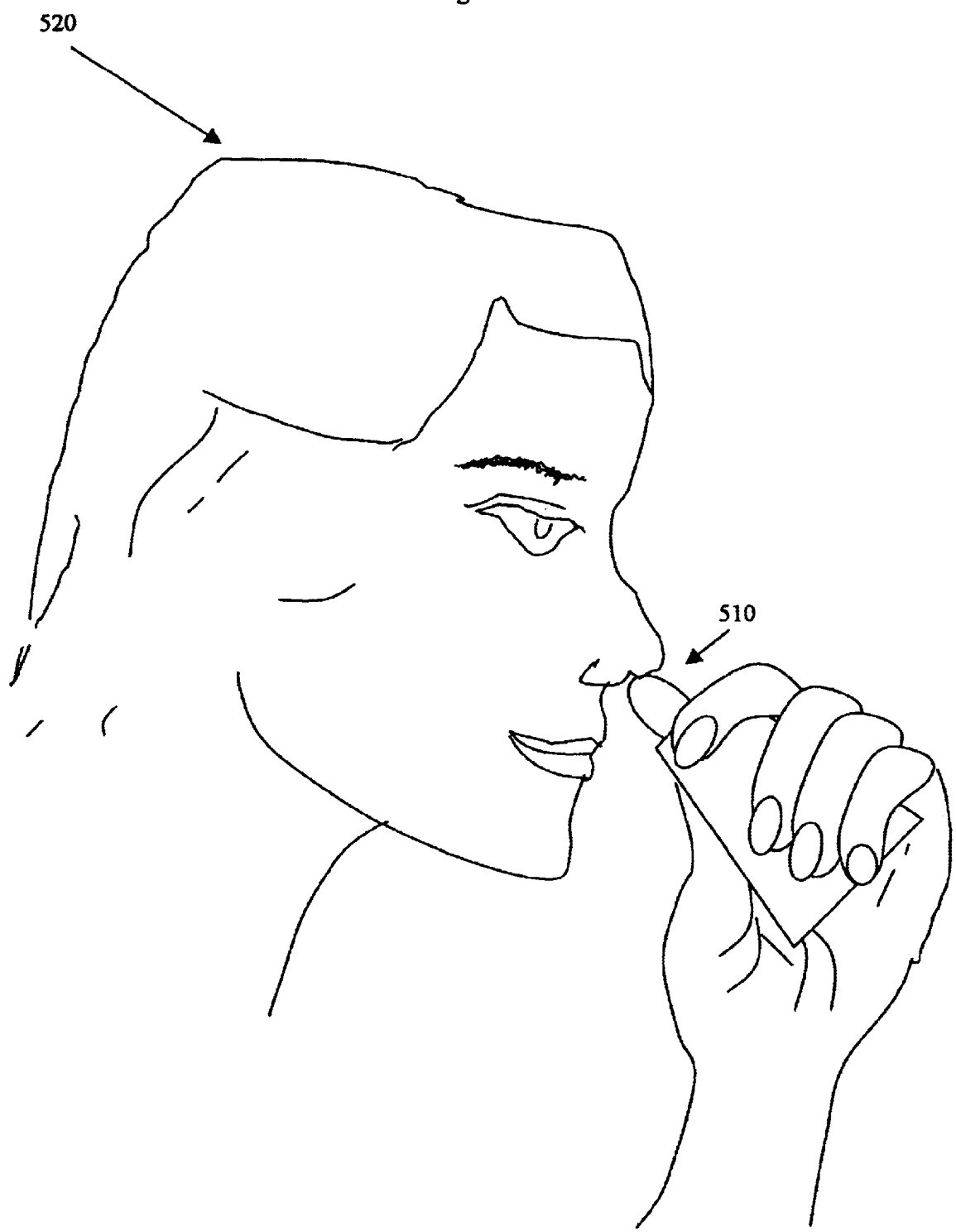
FIG. 5 shows a subject utilizing a spray bottle containing carbonated water.

Treatment of Allergic Rhinitis by Transmucosal Application of Capnic Nasal and Oral Spray Because of the observed similarity of the physiological effects of gaseous $CO_2$ and a capnic solution (carbonated water) applied to the skin, the inventors believed that a capnic solution might be effective for treatment of upper respiratory indications for which infusion of gaseous $CO_2$ is effective. With reference to FIG. 5, to test this hypothesis, a 70-ml commercially marketed plastic "squeeze" bottle 510 for dispensing a physiological saline spray was ¾ filled with fresh effervescing carbonated water. The carbonated water spray was then sprayed into the nose of a subject 520 who was suffering a mild allergic rhinitis attack. The inflammation and allergic distress were relieved immediately in a manner similar to that found when gaseous $CO_2$ was infused into the subject's nose. During the course of a day as allergic rhinitis attacks reoccurred, the carbonated water spray and gaseous $CO_2$ infusion were used alternately and their relative effectiveness assessed. The subject concluded that the two methods of treatment were equally effective for relief and suppression of allergic rhinitis symptoms.

Other subjects tried the spray once and also found it to give effective treatment. Those subjects resisted its further use, however, because all subjects found that the spray injection treatment is highly disagreeable compared with the gas infusion treatment and is no more effective. The disagreeable aspects cited were the discomfort associated with a liquid being sprayed up the nose and the messiness of the effluent liquid from the nose after the spray. Nevertheless, the carbonated nasal spray is a distinct alternative for treatment of the upper respiratory distress indications, and shares many of the advantages of a gaseous $CO_2$ infusion treatment including effectiveness, ease of use, rapid relief on demand, unlimited dose, low cost, and freedom from after-effects and other contraindications associated with the use of drugs. It is also possible to use the carbonated spray orally to deliver the dose of carbon dioxide to the mucous membranes in a similar manner.

The carbonated spray may offer superior treatment for patients suffering from dry nasal membranes along with allergy symptoms, i.e., the conditions for which the several saline nasal spray products presently are marketed. As with those products, a buffered isotonic solution should be used to minimize tissue volume changes by osmosis, but the solution should be carbonated by dissolving the maximum amount of $CO_2$ in it that is consistent with a practical operating pressure. The inventors found that the degree of carbonation of commercially marketed carbonated water corresponds to an acceptable $CO_2$ pressure in the spray bottle (1–2 $lb/in^2$ at room temperatures). Furthermore, it has been found that the carbonated water can be stored for an indefinitely long period when the screw cap (not shown) of the dispenser 510 is tightly closed. Multiple effective doses of the spray are obtained until almost complete exhaustion of the spray bottle contents.

Figure 6:
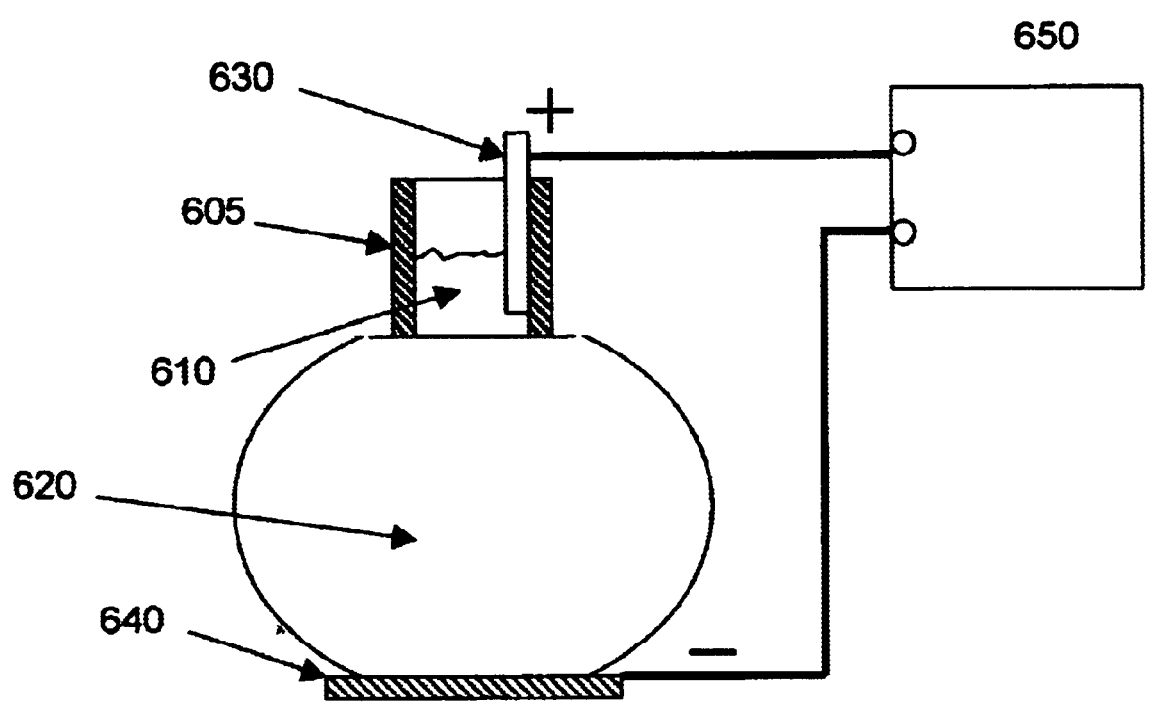
FIG. 6 shows a device used for obtaining a quantitative measurement of absorption of carbon dioxide in carbonated water through the skin of a human subject.

Measurement of the Electrical Potential Accompanying the Transcutaneous Application of a Capnic Solution With reference to FIG. 6, the inventors also undertook an experiment to obtain a quantitative indication of the extent and effect of transcutaneous infusion of $CO_2$ effected by applying a capnic aqueous solution (carbonated water) to the skin. In this experiment the inventors used a cylinder 605 of about 5 cm interior diameter, similar to that shown in FIG. 4, to apply about 2 cm of the capnic solution 610 to a subject's anterior thigh 620. The inventors then measured, using a digital logger 650, the resulting electrical potential difference between the liquid and the subject's body. As shown in FIG. 6, the potential difference was measured between a stainless steel electrode 630, immersed in a liquid pool (e.g. capnic solution) applied to the skin of the anterior thigh, and a large (15×25 cm) aluminum plate 640 (as indifferent electrode) applied to the moistened skin of the posterior thigh 620.

In all tests a hyperemia occurred over the area of contact between the skin and the applied pool of carbonated water. The skin was reddened to about the same degree and within about the same time of three to five minutes as was described in connection with the application of gaseous $CO_2$ to the skin. In control experiments comprising application of distilled water to the subjects' skin such reddening did not occur. Therefore, the inventors concluded that the hyperemia occurred as a result of $CO_2$ infusion into the skin.

Figure 7:
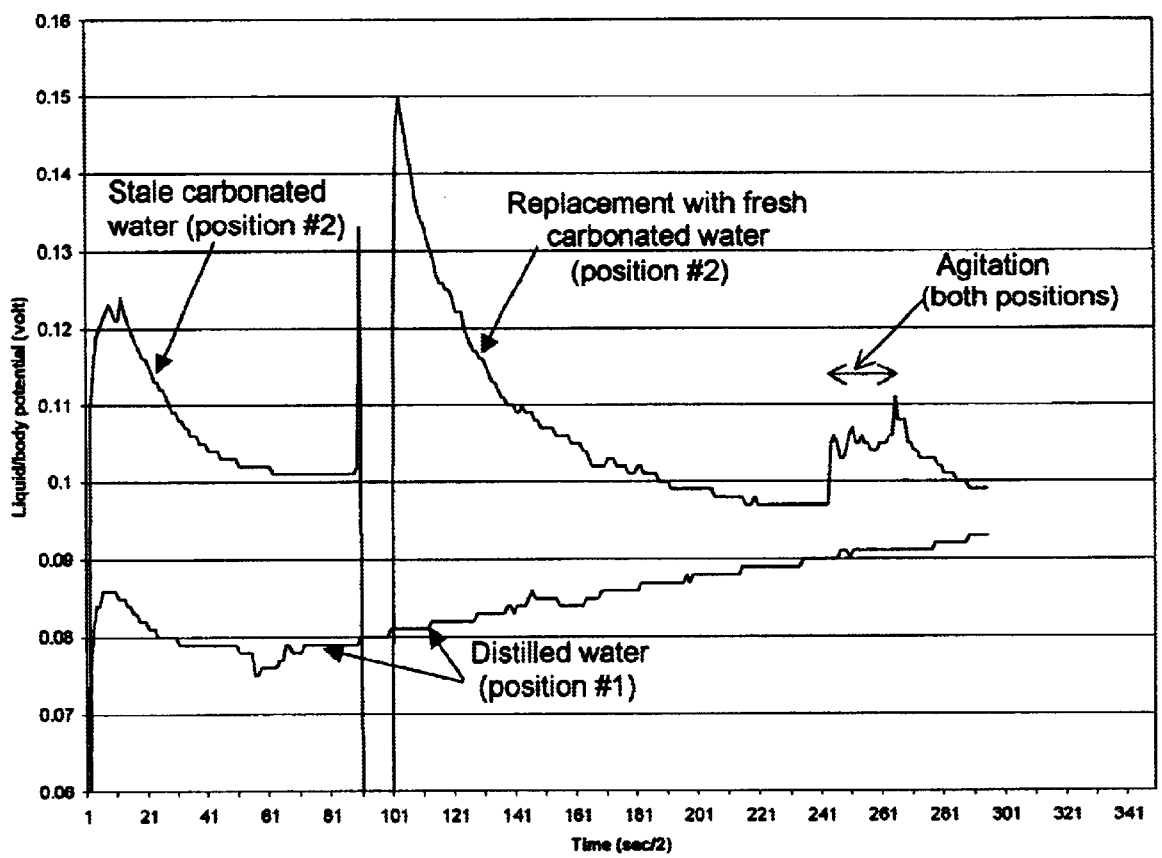
FIG. 7 shows the results of an experiment using the device of FIG. 6.
Figure 8:
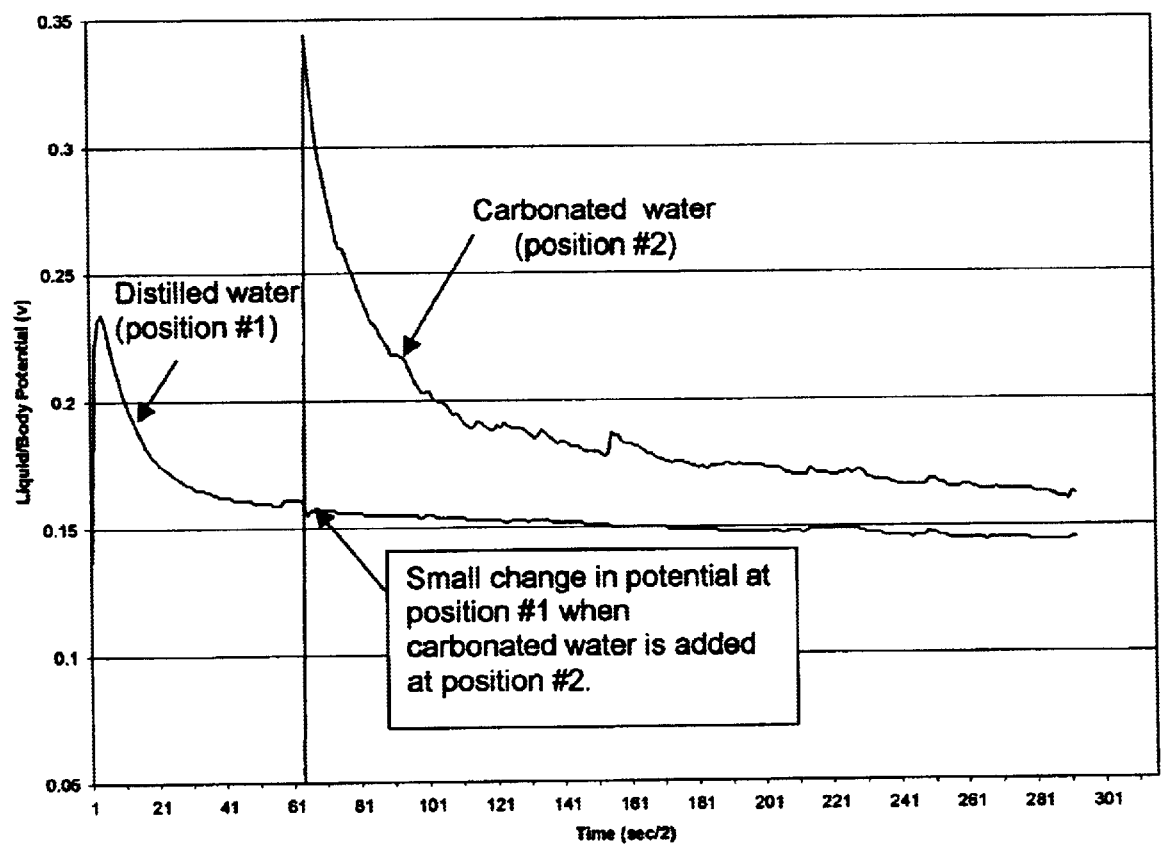
FIG. 8 shows the results of the same experiment as in FIG. 7, but taken immediately after the subject had been exercising.
Figure 9:
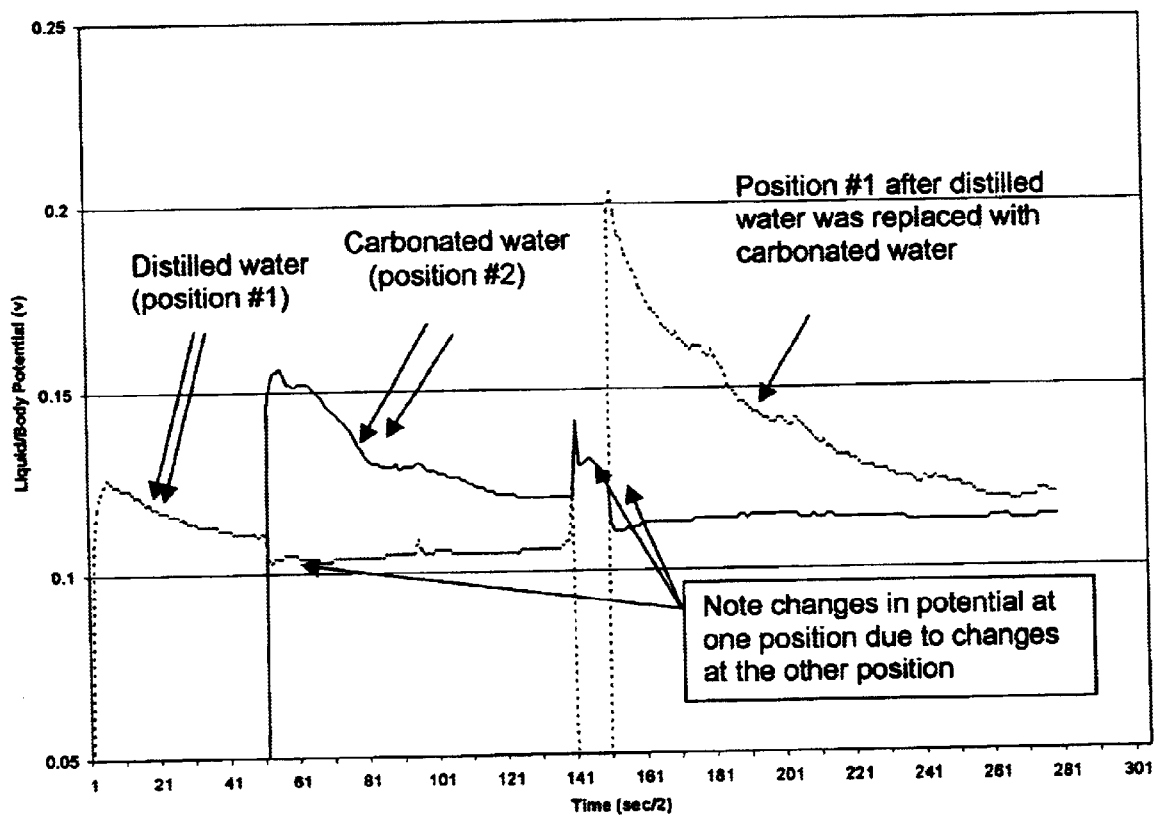
FIG. 9 shows the results of the experiment of FIG. 8 fifteen minutes after the measurements shown in FIG. 8.

FIGS. 7–9 show the changes in body/liquid potential difference after distilled water and carbonated water were applied simultaneously to adjacent regions of the skin of the anterior thigh. Both carbonated water and distilled water electrodes are spontaneously positive relative to the body electrode, i.e., such as to inhibit transport of carbonate or bicarbonate ions into the body from the capnic solution, or to expel them from the body into the distilled water.

Many observations have shown that the carbonated water potential and its change with time always are substantially greater than those for distilled water and that the changes are approximately equal to the cell resting potential (60–90 mv). Furthermore, as can be seen in FIG. 7, the potential is directly related to the concentration of the carbonated water (the "stale" solution shows no bubbles while the "fresh" solution effervesces and deposits bubbles onto the skin). There was an increase in potential when the carbonated water was agitated which suggests that the decrease in potential with time arises in part from a $CO_2$ concentration gradient in the carbonated water. No change occurs when the distilled water is agitated.

The decrease in carbonated water potential with time can arise from a decrease in its $CO_2$ concentration due to $CO_2$ diffusion into the skin, from a concentration gradient within the solution, and from an increase in the $CO_2$ concentration in the skin. The increase in potential upon agitation of the solution indicates that diffusion is primarily into the skin rather than into the atmosphere. Although not shown here, the $CO_2$ dose into the skin can be determined as a function of the decrease in the concentration of $CO_2$ in the agitated solution by various methods of measurement (e.g., conductivity, cell potential, pH or titration). By correlation of such measurements with the observed decrease in liquid/body potential, that decrease could be used as a convenient clinical method for dose determination.

The changes in distilled water potential can arise from changes in concentration of body fluids in the skin and in the applied liquid due to interdiffusion of the distilled water and the body fluid components, for example, by osmosis.

FIG. 8 shows data taken under the same conditions as those in FIG. 7 except that they are taken immediately after exercise. It can be seen that the potentials and associated changes with time are more than twice as large as those in FIG. 7. The data in FIG. 9, taken 15 minutes after those in FIG. 8, show a reversion to the behavior observed before exercise in FIG. 7. In addition, it can be seen that the application of $CO_2$ actually decreases the potential of the liquid applied on the skin in an adjacent region, whether that liquid is carbonated or distilled water. summary of the results of many such tests:

1. The liquid/body potential difference appears to be a quantitative measure of the concentration and delivered transcutaneous dose of $CO_2$ via carbonated water applied to the skin.
2. The ~3 minute exponential decay time of the liquid/body potential changes corresponds to the time for reddening of the skin by applied $CO_2$ and for the reddening of the skin to disappear, suggesting a 1:1 correlation of the observed potential and the physiological effects of $CO_2$ application.

3. Other factors affecting the underlying muscle, such as exercise, affect the liquid/body potential.
4. After the initial topical application of carbonated water, subsequent applications of carbonated water to the skin in one region of an underlying muscle affects the liquid/body potential in adjacent and non-adjacent regions of that muscle, suggesting that the effects of transcutaneous infusion of $CO_2$ are not confined to the skin in the immediate region of application.

The inventors conclude that a possible explanation for the observed results of the experiments described above is that the application of $CO_2$ to the skin changes the local electrical potential through a response of the local and adjacent tissue in opposition to an increase in the local physiological concentration of $CO_2$. This conclusion is supported by the observed reduced absorption of $CO_2$ in a physiologically active tissue, shown in FIG. 3, as compared with that in an equivalent passive system as shown in FIG. 2. This proposed mechanism is confirmed by the observed development of an electrical potential in opposition to the transport of carbonate and bicarbonate ions into the tissue as shown in FIGS. 7–9, and by the increase in this reaction potential due to increased partial pressure of $CO_2$ in the tissue resulting from exercise as shown in FIG. 8. Whatever the actual mechanism, the response to the application of $CO_2$ apparently is associated with a reduction of pain in the local and adjacent region of $CO_2$ application.

Implications for Therapeutic Use of $CO_2$

Gaseous $CO_2$

Figure 10:
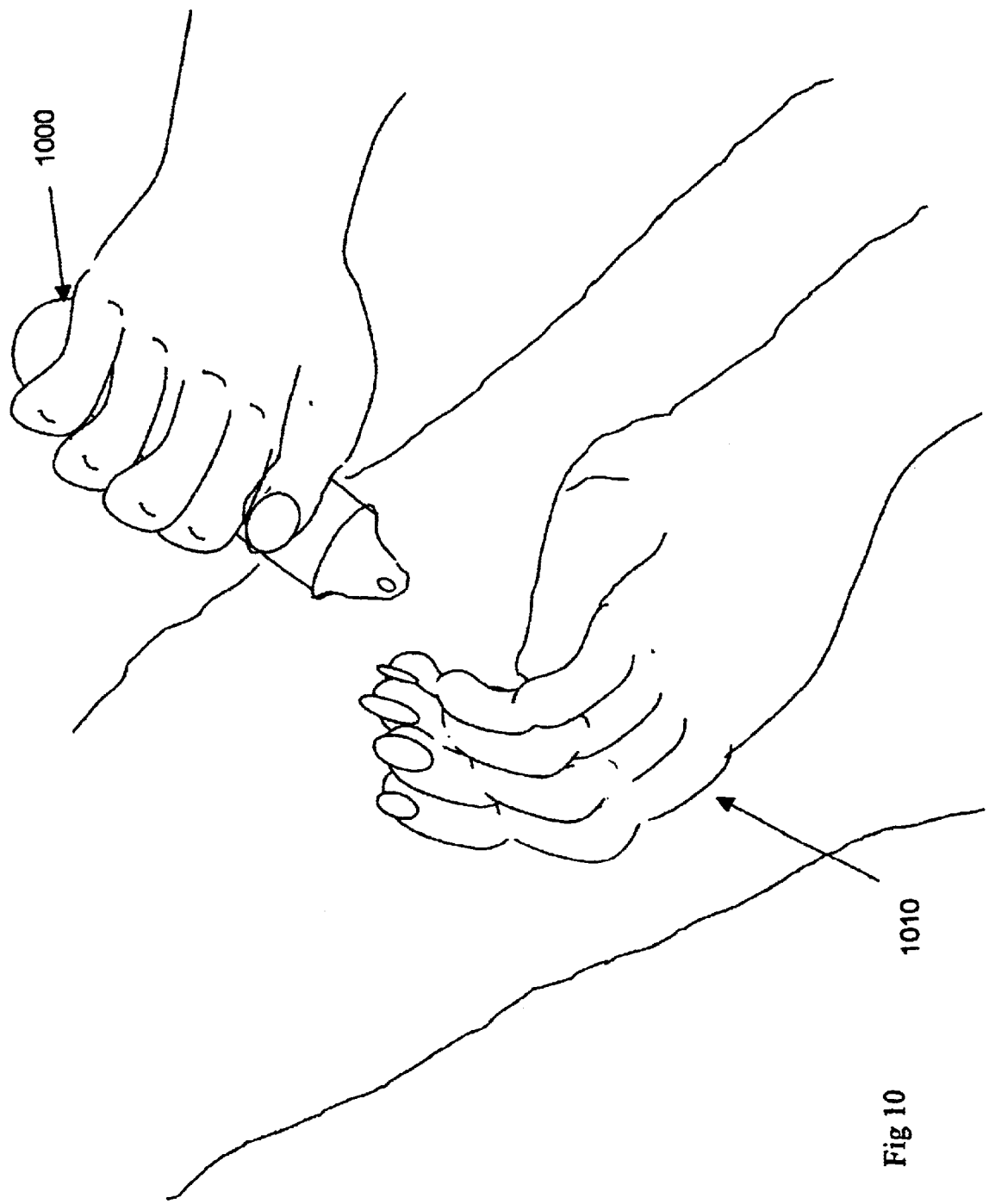
FIG. 10 shows a therapeutic application of gaseous carbon dioxide to an affected area of a subject.
Figure 11:
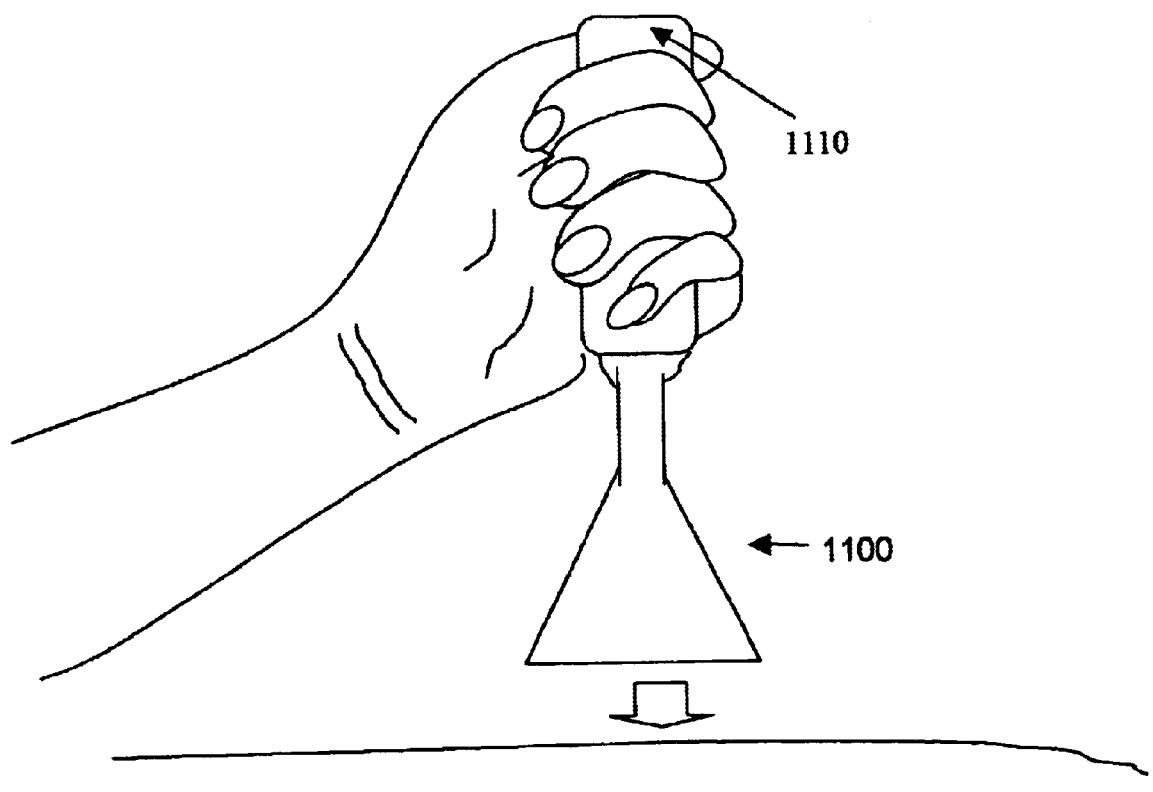
FIG. 11 shows another therapeutic application of gaseous carbon dioxide to an affected area of a subject using a cup device.

In therapeutic use, a subject would apply gaseous $CO_2$ to an affected area of the body. Application could be accomplished by a number of different apparatus. In the simplest application shown in FIG. 10, a dispensing device 1000 such as that shown in U.S. patent applications Ser. Nos. 09/614,389 and 09/708,186 for infusion of the nose, mouth or eyes could be used to bathe the affected area in $CO_2$. The flow rate for the devices of U.S. patent application Ser. No. 09/614,389 is as low as 2 to 10 cc/sec, although higher flow rates are possible with the same device. As shown in FIG. 10, the user could place a hand 1010 over the area forming a pocket between the hand and the area of skin. By infusing the $CO_2$ into the pocket, the rate at which the $CO_2$ is dispersed into the surrounding air will be reduced. Alternatively, as shown in FIG. 11, a cup 1100 or similar apparatus of appropriate size and shape could be used in conjunction with the source of $CO_2$ 1110 to retain the gas over the treated area. Preferably, the cup would be of a gas impermeable material to limit the loss of $CO_2$. Of course, the funnel apparatus used in the inventors' experiment to measure the rate of transcutaneous absorption of $CO_2$ could also be used with minimal modifications to accomplish the same purpose. With the cup or funnel, after placement on the affected area, the cup or funnel would be purged of air by a prolonged flow of $CO_2$. Unlike the experiment described previously, it would not be necessary to move the device after the purging procedure. The time of $CO_2$ application could vary from a few minutes to, if an attached cup or funnel device was used, a few hours.

The gas used for treatment should be essentially pure, that is, by volume, at least 50% carbon dioxide, preferably at least 70% carbon dioxide and more preferably 95% or greater. For certain applications, gases other than $CO_2$, drugs, surfactants or other substances could be incorporated into the flow.

Aqueous Solutions of $CO_2$

Figure 12:
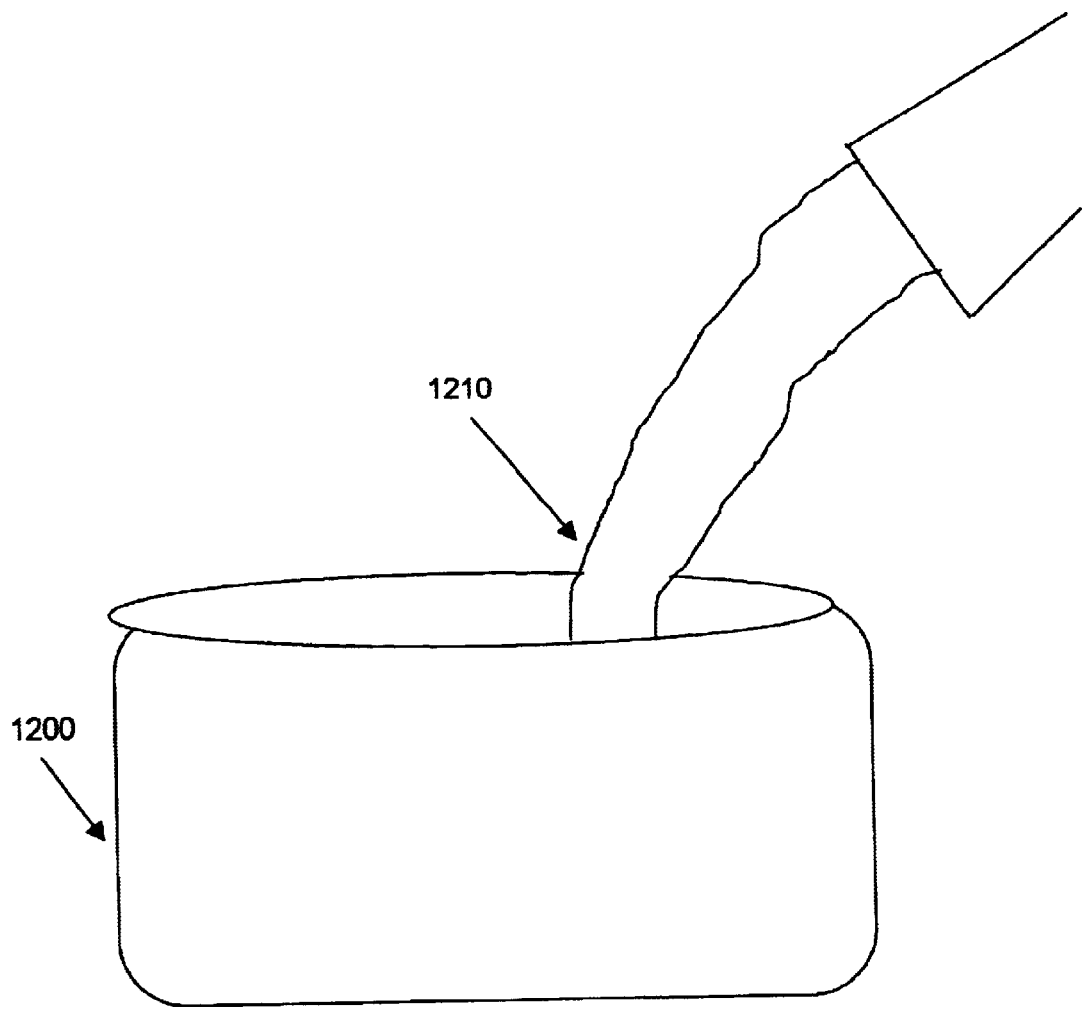
FIG. 12 shows a subject submerging an affected body part into carbonated water.

As suggested above, an aqueous solution of $CO_2$ can be used to relieve both localized and general pain through submersion of the affected areas. As shown in FIG. 12, the general procedure would be to place fresh, carbonated water (not shown) into a container or tub 1200 of appropriate size and have the subject submerge the area(s) to be treated in the carbonated water, for example, the hand and wrist 1210. The subject could vary the time of submersion from a few minutes, preferably at least three minutes, to a few hours, depending upon the severity of the pain and individual response to the treatment. Submersion of the whole body or substantially the whole body, i.e., the entire body except the head to allow for breathing, may be appropriate for certain treatments.

As an alternative, which is shown in FIG. 4, depending upon the size and location of the treated area, a device such as that used to test the subject response could be used. In other words, the fresh, carbonated water 430 could be contained in a $CO_2$ " patch," for example an open container or cylinder 410, and the container placed on the skin over an affected area.

For application to mucous membranes, such as the nose, mouth or ears, as shown in FIG. 5 the fresh carbonated water can be placed in a standard "squeeze" bottle 510, such as is used for nasal spray, or a modification thereof. To use, the subject would open the bottle, placed the bottle into a nostril or other orifice, and squeeze to produce a spray of the capnic solution. The bottle would then be closed tightly to preserve the carbonated water for later use.

$CO_2$ Patches

Figure 13:
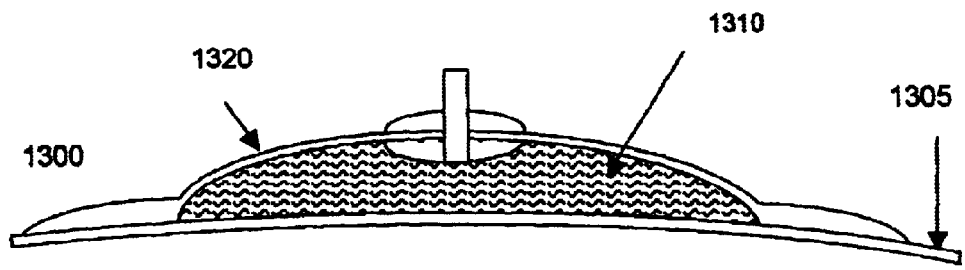
FIG. 13 shows embodiments of "patches" for application of liquid or gaseous $CO_2$.
Figure 14:
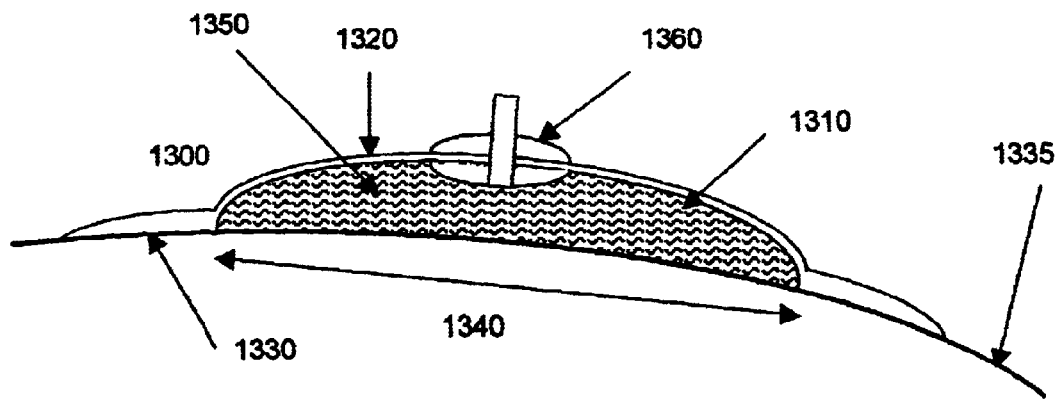
Figure 15:
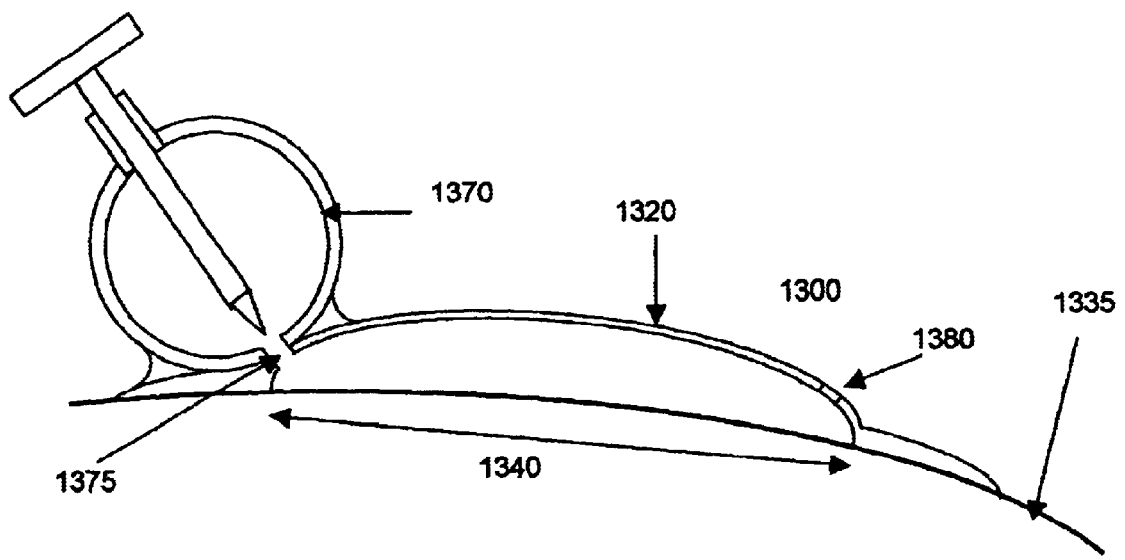
Figure 16:
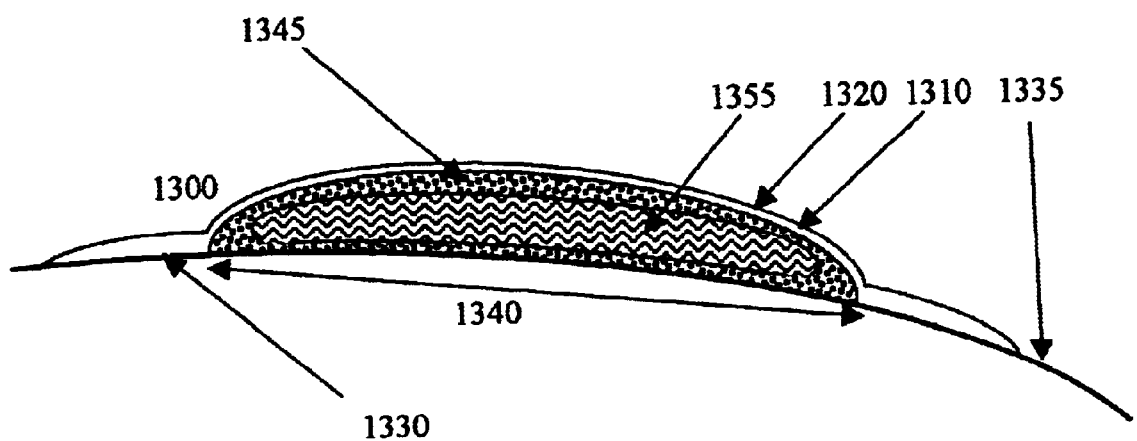

FIG. 13 shows "patch" embodiments by which $CO_2$ or other gaseous agents can be applied to the skin to relieve pain in a region of the body. FIG. A shows a patch 1300 with a peelable closure 1305 to contain and protect its active contents before use. FIG. B shows the patch 1300 with the peelable closure removed and applied to the skin to relieve pain in a region of the body. The patch 1300 consists of a cavity 1310 enclosed by a gas and liquid impermeable plastic envelope 1320 having an adhesive rim 1330 for attachment of the edge of the cavity to the skin 1335, thereby forming a gas-tight seal and chamber 1340. The chamber 1340 is filled with a sponge or other liquid-containing medium 1350 soaked with a gas-containing liquid. When the patch is in use this liquid is in contact with the skin and delivers a dose of the dissolved gaseous agent to the underlying tissue by transcutaneous diffusion as describe herein.

An electrode 1360 can be used to monitor the dose and its effect on the tissue by measurement of the electrical potential between this electrode and a conventional ECG electrode (not shown) elsewhere on the body, as described and shown in connection with FIGS. 7–9. Although an electrode as shown could be included for use in a clinical setting, it need not be a part of a patch intended solely for more general use.

As an alternative to the liquid containing medium 1350, the patch 1300 shown in FIGS. A and B the gas-containing liquid in the chamber 1340 can be replaced by an agent that generates the gas by a chemical reaction such as a mixture of solid citric acid and water-containing microcapsules, which when crushed together release a substantial quantity of carbon dioxide gas that then can diffuse through the skin as described. To facilitate diffusion of the gas from the chamber 1340 into the skin in this embodiment it is desirable to wet the skin before application of the patch or otherwise before the gas is applied to the skin. As shown in FIG. C, as an alternative to microcapsules, the chamber 1340 may include a porous envelope 1345 inside the gas and liquid impermeable envelope 1320 that contains the gas-generating agent 1355 to which water is added just prior to application of the patch 1300 to activate the gas generation process. In this alternative, the skin would not need not be moistened prior to use of the patch.

In the patch embodiment shown in FIG. D, a small cylinder 1370 containing the gaseous agent at low pressure is attached to the patch 1300 with a mechanism and port 1375 for its slow release into the patch chamber 1340. In this case it is necessary to provide a vent 1380 for escape of air as air is purged from the patch and to prevent overpressure within the chamber. Such a vent may be desirable in patch embodiments that utilize an agent for chemical generation of the gas. In the embodiment shown in FIG. D, it is desirable for the skin to be moistened prior to application of the patch to facilitate diffusion of the gaseous agent into the skin. As an alternative to moistening the skin with water prior to application, the chamber 1340 could be filled with a carbonated or plain water-soaked sponge or similar medium similar to the medium 1310, and gas from the attached cylinder would then used to maintain a high gas concentration in the water for long-term application.

The quantity of $CO_2$ required to achieve saturation of the skin is very small, so the required volume of carbonated water or gas-generating agent in the patch, or of gas in the cylinder, is easily contained in a conveniently-sized patch.

While preferred embodiments of the present invention are described above and in the following claims, it is contemplated that various modifications may be made without departing from the spirit and scope of the invention. Furthermore, many of the features of the various embodiments described herein can be combined or added to other devices to obtain the optimum combination of features for particular applications and markets.

What is claimed is:

1. A device for transcutaneous application of carbon dioxide comprising:

A gas impermeable sheet defining a perimeter and further comprising an adhesive placed around the perimeter, adapted for removable application to a subject's skin, to form a pocket between the subject's skin and the sheet;

An absorbent medium containing a carbon dioxide containing liquid, adapted to be placed inside the pocket;

Whereby the absorbent medium and the liquid may be placed against a subject's skin and held within the sheet to deliver a dose of carbon dioxide to the subject.

2. A device as set forth in claim 1 further comprising:

A vent in the sheet.

3. A device as set forth in claim 2 further comprising:

A port adapted for attachment to a source of carbon dioxide.

4. A device as set forth in claim 1 further comprising an electrode extending through the sheet, in contact with the carbon dioxide containing liquid and adapted for connection to an external meter.

* * * * *